United States Patent [19]
Toriyabe et al.

[11] Patent Number: 5,512,551
[45] Date of Patent: Apr. 30, 1996

[54] BENZOHYDROXYMOYLAZOLE DERIVATIVES AND INSECTICIDE INCLUDING THE SAME

[75] Inventors: Keiji Toriyabe; Takayoshi Takehi, both of Shizuoka; Yukio Nezu, Fujieda; Yuki Nakano, Shizuoka; Tomonori Shimazu, Hamamatsu, all of Japan

[73] Assignees: Kumiai Chemical Industry Co., Ltd.; Ihara Chemical Industry Co., Ltd., both of Tokyo, Japan

[21] Appl. No.: 281,039

[22] Filed: Jul. 27, 1994

Related U.S. Application Data

[62] Division of Ser. No. 915,817, Jul. 28, 1992, Pat. No. 5,366,988.

[30] Foreign Application Priority Data

Nov. 29, 1990 [JP] Japan ..................................... 2-331896
Jun. 5, 1991 [JP] Japan ..................................... 3-159834

[51] Int. Cl.$^6$ ............................ A01N 43/50; C07F 7/10; C07D 233/61
[52] U.S. Cl. ........................... 514/63; 514/399; 548/110; 548/336.1
[58] Field of Search ................................ 548/110, 336.1; 514/63, 399

[56] References Cited

U.S. PATENT DOCUMENTS 4,599,348  7/1986  Schmetzer et al. .................. 548/336.1

FOREIGN PATENT DOCUMENTS 1-308260  12/1989  Japan .

OTHER PUBLICATIONS

Hokari et al, "Preparation of hydroximoylinidozoles, etc." CA 116: 2318 (1991).

Primary Examiner—Patricia L. Morris
Attorney, Agent, or Firm—Oblon, Spivak, McClelland, Maier & Neustadt

[57] ABSTRACT

The present invention provides benzohydroximoylazole derivatives represented by the following novel formula:

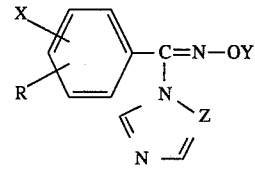

wherein R is a branched alkyl group having not fewer than 3 carbon atoms, a fluorine-substituted alkyl group having not fewer than 2 carbon atoms, a branched alkoxy group having not fewer than 3 carbon atoms, a halogen-substituted alkoxy group having not fewer than 3 carbon atoms, a cycloalkyl group, a cycloalkylmethyl group which may be substituted with one or two alkyl groups, a substituted silylalkyl group, a substituted silylalkyloxy group, a cycloalkyloxy group which may be substituted with one or two alkyl groups, an alkylthio group, a halogen-substituted alkyloxyalkyl group, an alkynyl group, or a halogen-substituted alkenyloxy group;
X is a hydrogen atom, a chlorine atom, or a fluorine atom; Y is an alkyl group; and Z is a nitrogen atom or a methyne group,
and methods for producing the same, insecticides including the benzohydroximoylazole derivatives as an active ingredient.

9 Claims, No Drawings

BENZOHYDROXYMOYLAZOLE DERIVATIVES AND INSECTICIDE INCLUDING THE SAME

RELATED APPLICATIONS

This application is a division of U.S. application Ser. No. 07/915,817 filed Jul. 28, 1992, now U.S. Pat. No. 5,366,988, which is a 371 of PCT/JP91/01614 on Nov. 25,1991.

FIELD OF THE INVENTION

The present invention relates to a benzohydroximoylazole derivative and to an insecticide containing the same as an active ingredient.

1. Background of the Invention

Heretofore, it has been known that compounds such as 1-(O-ethyl-4-butylbenzohydroximoyl)-1H-1,2,4-triazole and the like have insecticidal activities (for example, as described in Japanese Patent Application First Publication No. 1-308260).

2. Disclosure of the Invention

Such compounds disclosed in the above-mentioned patent application do not have the sufficient insecticidal effect. Recently, strains of harmful insects exhibiting resistance to conventional insecticides have appeared due to extensive and prolonged use thereof, and for this reason, the effectiveness of conventional insecticides are being lowered. In particular, the harmful insects in the order hemiptera such as the Delphacidae, Deltocephalidae, Aphididae, Pseudococcidae, Aleyrodidae, Pentatomidae, and the like have caused considerable damage to trees and to crops such as rice, wheat, potatoes, and the like.

Therefore, it is desirable to develop an insecticide having both superior insecticidal effect at low rates of application and effectiveness against the resistant strains of harmful insects described above.

The present inventors have synthesized various benzohydroximoylazole derivatives and have carried out extensive research in connection with the physiological activities thereof. As a result, they have found that the compounds according to the present invention wherein special substituents are bonded to the phenyl rings of the benzohydroximoylazole derivatives have extremely superior insecticidal activities against the various harmful insects, especially the harmful hemiptera such as Delphacidae, Deltocephalidae, Aphididae, Pentatomidae, and the like. The insecticidal activities of the compounds according to the present invention are superior to those of the compounds disclosed in Japanese Patent Application First Publication No. 1-308260. In addition, the compounds of the present invention exhibit improved insecticidal activities against the harmful resistant insects described above.

The present invention provides the following benzohydroximoylazol derivatives represented by formula [I] and an insecticide including the same as an active ingredient:

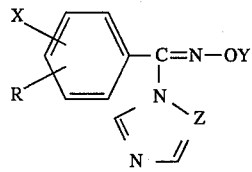

wherein R is a branched alkyl group having not fewer than 3 carbon atoms, a fluorine-substituted alkyl group having not fewer than 2 carbon atoms, a branched alkoxy group having not fewer than 3 carbon atoms, a halogen-substituted alkoxy group having not fewer than 3 carbon atoms, a cycloalkyl group, a cycloalkylmethyl group which may be substituted with one or two alkyl groups, a substituted silylalkyl group, a substituted silylalkyloxy group, a cycloalkyloxy group which may be substituted with one or two alkyl groups, an alkylthio group, a halogen-substituted alkyloxyalkyl group, an alkynyl group, or a halogen-substituted alkenyloxy group;

X is a hydrogen atom, a chlorine atom, or a fluorine atom;

Y is an alkyl group; and

Z is a nitrogen atom or a methyne group.

In formula [I], a branched alkyl group having not fewer than 3 carbon atoms includes, for example, isopropyl, isobutyl, s-butyl, t-butyl, isopentyl, 1-methylbutyl, 2-methylbutyl, neopentyl, isohexyl, 1-methylpentyl, 2-methylpentyl, 3-methylpentyl, 2,2-dimethylbutyl, 2,3-dimethylbutyl, 3,3-dimethylbutyl, 5-methylhexyl, 3,3-dimethylpentyl, 4,4-dimethylpentyl, 1,3,3-trimethylbutyl, 2,3,3-trimethylbutyl, 3,3-dimethylhexyl, 1,1,3,3-tetramethylbutyl, or the like.

A branched alkoxy group having not fewer than 3 carbon atoms includes, for example, isopropoxy, isobutoxy, s-atoms butoxy, t-butoxy, i-pentyloxy, neopentyloxy, 1-methylbutoxy, 2-methylbutoxy, 1,2-dimethylpropoxy, 2-ethylbutoxy, 2,2-dimethylbutoxy, 3,3-dimethylbutoxy, trimethylpropoxy, 2,2-dimethylpentyloxy, 1,3,3-trimethylbutoxy, 1-ethyl-2,2-dimethylpropoxy, 1-isopropoxy- 2-methylpropoxy, or the like.

A fluorine-substituted alkyl group having not fewer than 2 carbon atoms includes, for example, perfluoroethyl, perfluoropropyl, perfluoroisopropyl, perfluorobutyl, perfluoroisopentyl, 4,4,4-trifluoro-3,3-bis(trifluoromethyl)butyl, or the like.

A halogen-substituted alkoxy group having not fewer than 3 carbon atoms includes, for example, 4,4,4-trifluorobutoxy, 3-chloro-2,2-dimethylpropoxy, 1,1,2,3,3,3-hexafluoropropoxy, 2,2-bis(trifluoromethyl)propoxy, 3,3,3-trifluoro- 2,2-bis(trifluoromethyl)propoxy, 2,2,3,3,4,4,4-heptafluoro-1-methylbutoxy, or the like.

As a cycloalkyl group, cyclopropyl, cyclopentyl, cyclohexyl, or cycloheptyl may be employed.

A cycloalkylmethyl group which may be substituted with one or two alkyl groups includes cyclopropylmethyl, cyclopentylmethyl, 2-methylcyclopentylmethyl, 3-methylcyclopentylmethyl, cyclohexylmethyl, or 3,5-dimethylcyclohexylmethyl.

As a substituted silylalkyl group, trialkylsilylalkyl may be employed.

A substituted silylalkyloxy group includes trialkylsilylalkyloxy, dialkylmonoalkenylsilylalkyloxy, or dialkylmonochloro-substituted alkylsilylalkyloxy.

A cycloalkyloxy group which may be substituted with one or two alkyl groups includes cyclopropyloxy, cyclopentyloxy, 2-methylcyclohexyloxy, 3-methylcyclohexyloxy, 4-methylcyclohexyloxy, 2,3-dimethylcyclohexyloxy, or 2,5-dimethylcyclohexyloxy.

As an alkylthio group, 2-methylpropylthio or the like is employed.

A halogen-substituted alkyloxyalkyl group includes 1,1-bis (trifluoromethyl)ethoxymethyl or the like.

As an alkynyl group, 3,3-dimethyl-1-butynyl or the like is used.

An alkenyl group includes 3,3-dimethyl-1-butenyl or 1-hexenyl.

A halogen-substituted alkenyloxy group includes 2-bromo-1-chlorovinyloxy or the like.

In addition, an alkyl group employed in Y includes a linear or branched alkyl group having 1 to 4 carbon atoms, for example, a methyl group, an ethyl group, a propyl group, an isopropyl group, a butyl group, an isobutyl group, a s-butyl group, a t-butyl group, or the like.

In formula [I], it is preferable that R be a branched alkyl group having 3 to 8 carbon atoms, a branched alkoxy group having 3 to 7 carbon atoms, or a halogen-substituted alkoxy group having 3 to 7 carbon atoms; Y be an ethyl group, a propyl group; an isopropyl group, or a s-butyl group; and Z be a nitrogen atom.

The benzohydroximoylazole derivative represented by formula [I] includes two stereomers: syn and anti configurations. The compounds according to the present invention include not only each stereomer but also a mixture of the two stereomers in any ratio.

In addition, in the case where X in formula [I] has a saturated or unsaturated cycloparaffin group or an aliphatic hydrocarbon group in the substituent, there are the possibility that the compound represented by formula [I] has at least two stereomers. The present invention includes these stereomers.

Next, the compounds according to the present invention are listed in Table 1. The compound Nos. given in Table 1 will be referred to in the subsequent description.

TABLE 1

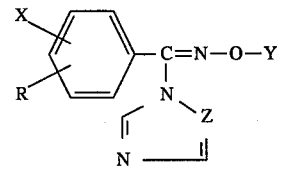

| Compound No. | R | X | Y | Z | Melting point (°C.) or Refractive index ($n^{20}_D$) |
|---|---|---|---|---|---|
| 1 | 3-$C_5H_{11}$-i | 4-F | $C_3H_7$-i | N | 1.5253 |
| 2 | 3-$OC_3H_7$-i | H | $C_3H_7$-i | N | 1.5390 |
| 3 | 3-$OC_4H_9$-i | H | $C_3H_7$-i | N | 1.5341 |
| 4 | 3-$OC_4H_9$-s | H | $C_3H_7$-i | N | 1.5320 |
| 5 | 3-$OCH(CH_3)CH_2CH_2CH_3$ | H | $C_3H_7$-i | N | 1.5312 |
| 6 | 3-$OCH_2CH(CH_3)CH_2CH_3$ | H | $C_3H_7$-i | N | 1.5177 |
| 7 | 3-$OC_5H_{11}$-i | H | $C_3H_7$-i | N | 1.5341 |
| 8 | 3-$C_4H_9$-i | H | $C_3H_7$-i | N | 1.5360 |
| 9 | 3-$C_5H_{11}$-i | H | $C_3H_7$-i | N | 1.5317 |
| 10 | 3-$C_4H_9$-s | H | $C_3H_7$-i | N | 1.5338 |
| 11 | 3-$CH_2CH(CH_3)CH_2CH_3$ | H | $C_3H_7$-i | N | 1.5370 |
| 12 | 3-$C_3H_7$-i | H | $C_3H_7$-i | N | 1.5398 |
| 13 | 3-$C_4H_9$-t | H | $C_3H_7$-i | N | 1.5312 |
| 14 | 3-$OCH_2CH(C_2H_5)_2$ | H | $C_3H_7$-i | N | 1.5328 |
| 15 | 3-$CH(CH_3)CH_2CH_2CH_3$ | H | $C_3H_7$-i | N | 1.5317 |
| 16 | 3-$CH_2CH(CH_3)CH_2CH_2CH_3$ | H | $C_3H_7$-i | N | 1.5309 |
| 17 | 3-$CH(CH_3)CH_2CH_2CH_2CH_3$ | H | $C_3H_7$-i | N | 1.5205 |
| 18 | 3-$CH_2CH_2CH(CH_3)CH_2CH_3$ | H | $C_3H_7$-i | N | 1.5293 |
| 19 | 3-$OCH_2CH_2C(CH_3)_3$ | H | $C_3H_7$-i | N | 1.5289 |
| 20 | 3-$CH_2CH(CH_3)CH(CH_3)_2$ | H | $C_3H_7$-i | N | 1.5304 |
| 21 | 3-$C_5H_{11}$-i | 2-F | $C_3H_7$-i | N | 1.5202 |
| 22 | 3-$C_5H_{11}$-i | 4-F | $C_3H_7$-i | N | 1.5211 |
| 23 | 5-$C_5H_{11}$-i | 2-F | $C_3H_7$-i | N | 1.5202 |
| 24 | 3-$C_6H_{13}$-i | H | $C_3H_7$-i | N | 1.5198 |
| 25 | 5-$C_5H_{11}$-i | 2-Cl | $C_3H_7$-i | N | 1.5360 |
| 26 | 3-$OCH(CH_3)CF_2CF_2CF_3$ | H | $C_3H_7$-i | N | 1.4760 |
| 27 | 5-$OCH(CH_3)CF_2CF_2CF_3$ | 2-Cl | $C_3H_7$-i | N | 1.4919 |
| 28 | 5-$C_6H_{13}$-i | 2-Cl | $C_3H_7$-i | N | 1.5252 |
| 29 | 3-$OCH(CH_3)CH_2C(CH_3)_3$ | H | $C_3H_7$-i | N | 1.5108 |
| 30 | 3-$C(CH_3)_2CH_2C(CH_3)_3$ | H | $C_3H_7$-i | N | 1.5230 |
| 31 | 3-$C_7H_{15}$-i | 4-F | $C_3H_7$-i | N | 1.5147 |
| 32 | 3-$C_5H_{11}$-i | 4-F | $C_3H_7$-i | CH | 1.5258 |
| 33 | 3-$C_6H_{13}$-i | 4-F | $C_3H_7$-i | N | 1.5132 |
| 34 | 3-$C_6H_{13}$-i | 4-F | $C_3H_7$-i | CH | 1.5230 |
| 35 | 3-$OC_4H_9$-i | H | $C_3H_7$-i | CH | 1.5400 |
| 36 | 3-$OC_5H_{11}$-i | H | $C_3H_7$-i | CH | 1.5358 |
| 37 | 3-$CH_2C(CH_3)_3$ | H | $C_3H_7$-i | N | 1.5248 |
| 38 | 3-$OC_4H_9$-t | H | $C_3H_7$-i | N | 1.5308 |
| 39 | 5-$C_6H_{13}$-i | 2-F | $C_3H_7$-i | N | 1.5162 |
| 40 | 5-$C_6H_{13}$-i | 2-F | $C_3H_7$-i | CH | 1.5225 |
| 41 | 3-$C_5H_{11}$-i | H | $CH_3$ | N | 1.5422 |
| 42 | 3-$C_5H_{11}$-i | H | $C_4H_9$-s | N | 1.5293 |
| 43 | 3-$C_5H_{11}$-i | H | $C_2H_5$ | N | 1.5326 |
| 44 | 3-$OCH_2C(CH_3)_3$ | H | $C_3H_7$-i | N | 1.5202 |
| 45 | 3-$C_5H_{11}$-i | H | $C_4H_9$ | N | 1.5290 |

TABLE 1-continued $$\text{structure: } X, R\text{-substituted phenyl}-C(=N-O-Y)-N(Z)-CH=N \text{ (ring)}$$

| Compound No. | R | X | Y | Z | Melting point (°C.) or Refractive index ($n^{20}_D$) |
|---|---|---|---|---|---|
| 46 | 3-CH$_2$CH$_2$C(CH$_3$)$_3$ | H | C$_3$H$_7$-i | N | 1.5258 |
| 47 | 3-OCH$_2$C(CH$_3$)$_2$CH$_2$CH$_3$ | H | C$_3$H$_7$-i | N | 1.5269 |
| 48 | 3-C$_5$H$_{11}$-i | H | C$_3$H$_7$ | N | 1.5320 |
| 49 | 3-OCF$_2$CHFCF$_3$ | H | C$_3$H$_7$-i | N | 1.4809 |
| 50 | 3-OCH$_2$C(CH$_3$)$_3$ | H | C$_3$H$_7$-i | CH | 1.5340 |
| 51 | 3-OCH(CH$_3$)C(CH$_3$)$_3$ | H | C$_3$H$_7$-i | N | 1.5273 |
| 52 | 3-OCH$_2$C(CH$_3$)$_3$ | H | C$_2$H$_5$ | N | 1.5372 |
| 53 | 3-OCH$_2$C(CH$_3$)$_3$ | H | C$_4$H$_9$-s | N | 1.5276 |
| 54 | 3-C$_6$H$_{13}$-i | 2-F | C$_3$H$_7$-i | N | 1.5173 |
| 55 | 3-CH$_2$CH$_2$CH$_2$C(CH$_3$)$_3$ | H | C$_3$H$_7$-i | N | 1.5255 |
| 56 | 3-OCH$_2$CH$_2$CH$_2$CF$_3$ | H | C$_3$H$_7$-i | N | 1.5088 |
| 57 | 3-C$_5$H$_{11}$-i | H | C$_4$H$_9$-i | N | 1.5288 |
| 58 | 3-CH$_2$CH$_2$CH$_2$C(CH$_3$)$_3$ | H | C$_4$H$_9$-s | N | 1.5229 |
| 59 | 3-CH$_2$CH$_2$CH$_2$C(CH$_3$)$_3$ | H | C$_3$H$_7$ | N | 1.5268 |
| 60 | 3-OCH$_2$C(CH$_3$)$_2$CH$_2$CH$_3$ | H | C$_3$H$_7$-i | N | 1.5271 |
| 61 | 3-OCH$_2$C(CH$_3$)$_3$ | H | C$_3$H$_7$ | N | 45 ~ 46 |
| 62 | 3-CH$_2$CH$_2$C(CH$_3$)$_3$ | H | C$_4$H$_9$-s | N | 1.5261 |
| 63 | 3-CH$_2$CH$_2$C(CH$_3$)$_3$ | H | C$_2$H$_5$ | N | 1.5347 |
| 64 | 3-CH$_2$CH$_2$C(CH$_3$)$_3$ | H | C$_4$H$_9$-s | CH | 1.5313 |
| 65 | 3-CH$_2$CH$_2$C(CH$_3$)$_3$ | H | C$_2$H$_5$ | CH | 1.5401 |
| 66 | 3-OCH$_2$C(CH$_3$)$_2$CH$_2$Cl | H | C$_3$H$_7$-i | N | 1.5440 |
| 67 | 3-CH$_2$CH$_2$C(CH$_3$)$_3$ | H | C$_3$H$_7$ | N | 1.5305 |
| 68 | 3-CH$_2$CH$_2$C(CH$_3$)$_3$ | 4-F | C$_3$H$_7$-i | N | 1.5183 |
| 69 | 3-CH$_2$CH$_2$C(CH$_3$)$_3$ | H | C$_4$H$_9$-t | N | 1.5238 |
| 70 | 3-OCH$_2$C(CH$_3$)$_2$CH$_2$CH$_3$ | H | C$_3$H$_7$ | N | 1.5290 |
| 71 | 3-CH$_2$CH$_2$C(CH$_3$)$_3$ | H | C$_3$H$_7$-i | CH | 1.5326 |
| 72 | 3-OCH$_2$C(CH$_3$)$_2$CH$_2$CH$_3$ | H | C$_3$H$_7$ | N | 1.5300 |
| 73 | 3-OCH(CH$_3$)C(CH$_3$)$_3$ | H | C$_3$H$_7$ | N | 1.5327 |
| 74 | 3-CH$_2$CH$_2$C(CH$_3$)$_2$CH$_2$CH$_3$ | H | C$_3$H$_7$ | N | 1.5249 |
| 75 | 5-CH$_2$CH$_2$C(CH$_3$)$_2$CH$_2$CH$_3$ | 2-F | C$_3$H$_7$ | N | 1.5233 |
| 76 | 3-CH$_2$CH$_2$C(CH$_3$)$_3$ | 4-F | C$_3$H$_7$ | N | 1.5171 |
| 77 | 3-OCH$_2$C(CH$_3$)$_2$ | 4-F | C$_3$H$_7$ | N | 1.5203 |
| 78 | 3-CH$_2$C(CH$_3$)$_2$CH$_2$CH$_3$ | H | C$_3$H$_7$-i | N | 1.5306 |
| 79 | 5-CH$_2$CH$_2$C(CH$_3$)$_3$ | 2-F | C$_3$H$_7$-i | N | 1.5168 |
| 80 | 3-C$_5$H$_{11}$-i | 4-F | C$_3$H$_7$ | N | 1.5214 |
| 81 | 3-C$_5$H$_{11}$-i | 4-F | C$_2$H$_5$ | N | 1.5262 |
| 82 | 3-OCH$_2$C(CH$_3$)$_3$ | 4-F | C$_3$H$_7$-i | N | 1.5198 |
| 83 | 5-CH$_2$CH$_2$C(CH$_3$)$_3$ | 2-F | C$_3$H$_7$ | N | 1.5068 |
| 84 | 3-OCH(CH$_3$)CH$_2$CH(CH$_3$)$_2$ | H | C$_3$H$_7$-i | N | 1.5262 |
| 85 | 3-OCH(CH$_3$)CH$_2$CH(CH$_3$)$_2$ | H | C$_3$H$_7$ | N | 1.5293 |
| 86 | 3-OCH(CH$_3$)CH(CH$_3$)$_2$ | H | C$_3$H$_7$-i | N | 1.5327 |
| 87 | 5-CH$_2$CH$_2$C(CH$_3$)$_3$ | 2-Cl | C$_3$H$_7$-i | N | 1.5292 |
| 88 | 5-CH$_2$CH$_2$C(CH$_3$)$_3$ | 2-Cl | C$_3$H$_7$ | CH | 1.5360 |
| 89 | 3-OCH(CH$_3$)CH(CH$_3$)$_2$ | H | C$_3$H$_7$ | N | 1.5352 |
| 90 | 3-CH$_2$CH$_2$C(CH$_3$)$_3$ | 4-Cl | C$_3$H$_7$-i | N | 1.5338 |
| 91 | 5-CH$_2$CH$_2$C(CH$_3$)$_3$ | 2-F | C$_3$H$_7$ | CH | 1.5233 |
| 92 | 3-CH(CH$_3$)CH$_2$C(CH$_3$)$_3$ | H | C$_3$H$_7$-i | N | |
| 93 | 3-CH(CH$_3$)CH$_2$C(CH$_3$)$_3$ | H | C$_3$H$_7$ | N | |
| 94 | 3-CH$_2$CH(CH$_3$)C(CH$_3$)$_3$ | H | C$_3$H$_7$-i | N | |
| 95 | 3-CH$_2$CH(CH$_3$)C(CH$_3$)$_3$ | H | C$_3$H$_7$ | N | |
| 96 | 3-CH$_2$CH$_2$C(CH$_3$)$_2$CH$_2$CH$_3$ | H | C$_3$H$_7$-i | N | |
| 97 | 3-CH$_2$CH$_2$C(CF$_3$)$_3$ | H | C$_3$H$_7$-i | N | |
| 98 | 5-CH$_2$CH$_2$C(CF$_3$)$_3$ | 2-F | C$_3$H$_7$-i | N | |
| 99 | 3-OCH(C$_2$H$_5$)C(CH$_3$)$_3$ | H | C$_3$H$_7$ | N | 1.5305 |
| 100 | 3-OCH(C$_2$H$_5$)C(CH$_3$)$_3$ | H | C$_3$H$_7$-i | N | 1.5274 |
| 101 | 3-OCH$_2$C(CH$_3$)(CF$_3$)$_2$ | H | C$_3$H$_7$ | N | |
| 102 | 3-OCH$_2$C(CH$_3$)(CF$_3$)$_2$ | H | C$_3$H$_7$-i | N | 1.4852 |
| 103 | 3-OCH$_2$C(CF$_3$)$_3$ | H | C$_3$H$_7$ | N | |
| 104 | 3-OCH$_2$C(CF$_3$)$_3$ | H | C$_3$H$_7$-i | N | |
| 105 | 5-OCH$_2$C(CH$_3$)$_3$ | 2-F | C$_3$H$_7$ | N | |
| 106 | 5-OCH$_2$C(CH$_3$)$_3$ | 2-F | C$_3$H$_7$-i | N | |
| 107 | 5-OCH$_2$C(CH$_3$)(CF$_3$)$_2$ | 2-F | C$_3$H$_7$ | N | |
| 108 | 5-OCH$_2$C(CH$_3$)(CF$_3$)$_2$ | 2-F | C$_3$H$_7$-i | N | |
| 109 | 5-OCH$_2$C(CF$_3$)$_3$ | 2-F | C$_3$H$_7$ | N | |
| 110 | 5-OCH$_2$C(CF$_3$)$_3$ | 2-F | C$_3$H$_7$-i | N | |

TABLE 1-continued

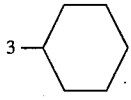

| Compound No. | R | X | Y | Z | Melting point (°C.) or Refractive index ($n^{20}_D$) |
|---|---|---|---|---|---|
| 111 | 3-OCH$_2$C(CH$_3$)(CF$_3$)$_2$ | 4-F | C$_3$H$_7$ | N | |
| 112 | 3-OCH$_2$C(CH$_3$)(CF$_3$)$_2$ | 4-F | C$_3$H$_7$-i | N | |
| 113 | 3-OCH$_2$C(CF$_3$)$_2$ | 4-F | C$_3$H$_7$ | N | |
| 114 | 3-OCH$_2$C(CF$_3$)$_3$ | 4-F | C$_3$H$_7$-i | N | |
| 115 | 3-CH$_2$CH$_2$C(CH$_3$)$_3$ | H | C$_4$H$_9$-i | N | 1.5248 |
| 116 | 3-CH$_2$CH$_2$C(CH$_3$)$_3$ | H | C$_5$H$_{11}$-i | N | 1.5222 |
| 117 | 3-OCH(CH(CH$_3$)$_2$)$_2$ | H | C$_3$H$_7$ | CH | 1.5301 |
| 118 | 3-OCH$_2$C(CH$_3$)$_3$ | H | C$_3$H$_7$ | CH | 1.5339 |
| 119 | 3-CH$_2$CH$_2$C(CH$_3$)$_3$ | H | CH$_3$ | N | 1.5398 |
| 120 | 3-OC$_4$H$_9$-i | 4-F | C$_3$H$_7$-i | N | 44 ~ 45 |
| 121 | 3-OC$_4$H$_9$-i | 4-F | C$_3$H$_7$ | N | 61 ~ 63 |
| 122 | 5-CH$_2$CH$_2$CH(CH$_3$)CH$_2$CH$_3$ | 2-F | C$_4$H$_9$-i | N | 1.5152 |
| 123 | 3-C$_2$F$_5$ | H | C$_3$H$_7$-i | N | 1.5921 |
| 124 | 3-C$_3$F$_7$ | H | C$_3$H$_7$-i | N | 1.4738 |
| 125 | 3-C$_4$H$_9$ | H | C$_3$H$_7$-i | N | 1.4633 |
| 126 | 5-CH$_2$CH$_2$C(CH$_3$)$_3$ | 2-F | CH$_3$ | N | |
| 127 | 5-CH$_2$CH$_2$C(CH$_3$)$_3$ | 2-F | C$_2$H$_5$ | N | |
| 128 | 5-CH$_2$CH$_2$C(CH$_3$)$_3$ | 2-F | C$_4$H$_9$-i | N | |
| 129 | 5-CH$_2$CH$_2$C(CH$_3$)$_3$ | 2-F | C$_4$H$_9$-t | N | |
| 130 | 5-C(CH$_3$)$_3$ | 2-F | C$_3$H$_7$-i | N | |
| 131 | 5-C$_4$H$_9$-t | 2-F | C$_3$H$_7$-i | N | |
| 132 | 5-(CH$_2$)$_3$C(CH$_3$)$_3$ | 2-F | C$_3$H$_7$-i | N | |
| 133 | 5-C$_4$H$_9$-t | 2-F | C$_3$H$_7$ | N | |
| 134 | 5-CH$_2$C(CH$_3$)$_3$ | 2-F | C$_3$H$_7$ | N | |
| 135 | 5-(CH$_2$)$_3$C(CH$_3$)$_3$ | 2-F | C$_3$H$_7$ | N | |
| 136 | 3-CF$_2$CF$_2$CF(CF$_3$)$_2$ | H | C$_3$H$_7$ | N | |
| 137 | 3-CF$_2$CF$_2$CF(CF$_3$)$_2$ | H | C$_3$H$_7$-i | N | 1.4498 |
| 138 | 3-CF(CF$_3$)$_2$ | H | C$_3$H$_7$ | N | |
| 139 | 3-CF(CF$_3$)$_2$ | H | C$_3$H$_7$-i | N | |
| 140 | 3-OCH$_2$Si(CH$_3$)$_3$ | H | C$_3$H$_7$-i | N | 1.5310 |
| 141 | 3-OCH$_2$Si(CH$_3$)$_2$CH$_2$CH$_3$ | H | C$_3$H$_7$-i | N | 1.5321 |
| 142 | 3-OCH$_2$Si(CH$_3$)$_2$CH=CH$_2$ | H | C$_3$H$_7$-i | N | 1.5373 |
| 143 | 3-OCH$_2$Si(CH$_3$)$_2$CH$_2$Cl | H | C$_3$H$_7$-i | N | 1.5453 |
| 144 | 3-OCH$_2$Si(CH$_3$)$_3$ | H | C$_3$H$_7$-i | CH | 1.5352 |
| 145 | 3-OCH(CH$_3$)Si(CH$_3$)$_3$ | H | C$_3$H$_7$-i | N | 1.5252 |
| 146 | 3-OCH$_2$Si(CH$_3$)$_3$ | H | CH$_3$ | N | 1.5430 |
| 147 | 3-OCH$_2$Si(CH$_3$)$_3$ | H | C$_2$H$_5$ | N | 1.5385 |
| 148 | 3-OCH$_2$Si(CH$_3$)$_3$ | H | C$_4$H$_9$ | N | 1.5248 |
| 149 | 3-OCH$_2$Si(CH$_3$)$_3$ | H | C$_4$H$_9$-s | N | 1.5301 |
| 150 | 3-OCH$_2$Si(CH$_3$)$_3$ | H | C$_4$H$_9$-t | N | 1.5216 |
| 151 | 3-OC$_2$H$_4$Si(CH$_3$)$_3$ | H | C$_3$H$_7$-i | N | 1.5288 |
| 152 | 5-OCH$_2$Si(CH$_3$)$_3$ | 2-Cl | C$_3$H$_7$-i | N | 1.5342 |
| 153 | 3-cyclohexyl | H | C$_3$H$_7$-i | N | 49–51 |
| 154 | 3-CH$_2$-cyclopentyl | H | C$_3$H$_7$-i | N | 1.5499 |
| 155 | 3-CH$_2$-cyclohexyl | H | C$_3$H$_7$-i | N | 34–37 |

TABLE 1-continued

[Structure: phenyl ring with X and R substituents, bearing C(=N-O-Y)-N(Z)-CH=N cyclic group]

| Compound No. | R | X | Y | Z | Melting point (°C.) or Refractive index ($n^{20}_D$) |
|---|---|---|---|---|---|
| 156 | 3-CH₂-cyclohexyl(1,3-diCH₃) | H | C₃H₇-i | N | 1.5350 |
| 157 | 3-CH₂-cyclopentyl(CH₃) | H | C₃H₇-i | N | 1.5098 |
| 158 | 3-O-cyclohexyl | H | C₃H₇-i | N | 1.5490 |
| 159 | 3-O-cyclohexyl(2-CH₃) | H | C₃H₇-i | N | 1.5430 |
| 160 | 3-O-cyclohexyl(3-CH₃) | H | C₃H₇-i | N | 1.5443 |
| 161 | 3-O-cyclohexyl(4-CH₃) | H | C₃H₇-i | N | 1.5438 |
| 162 | 3-CH₂OC(CF₃)₂CH₃ | H | C₃H₇-i | N | 1.4821 |
| 163 | 3-CH₂OC(CH₃)₂CF₃ | H | C₃H₇-i | N | 1.5012 |
| 164 | 3-SCH₂CH(CH₃)₂ | H | C₃H₇-i | N | 1.5551 |
| 165 | 3-SCH₂CH(CH₃)₂ | H | C₃H₇-i | CH | 1.5675 |
| 166 | 3-C≡CC(CH₃)₃ | H | C₃H₇-i | N | 1.5495 |
| 167 | 3-C≡CC(CH₃)₃ | 4-F | C₃H₇-i | N | 1.5431 |
| 168 | 3-CH=CHC(CH₃)₃ | H | C₃H₇-i | N | 1.5409 |
| 169 | 3-CH=CHCH₂CH₂CH₃ | H | C₃H₇-i | N | 1.5432 |
| 170 | 3-CH=CHCH(CH₃)₂ | H | C₃H₇-i | N | 1.5540 |
| 171 | 3-OCF=CHBr | | C₃H₇-i | N | 1.5531 |
| 172 | 3-OCH₂Si(CH₃)₃ | H | C₃H₇ | N | 1.5348 |
| 173 | 3-O-cyclohexyl(2,3-diCH₃) | H | C₃H₇-i | N | 1.5438 |
| 174 | 5-CH₂OC(CF₃)₂CH₃ | 2-F | C₃H₇-i | N | 69–74 |
| 175 | 3-CH₂OC(CF₃)₂CH₃ | 2-F | C₃H₇-i | N | 38–43 |

TABLE 1-continued

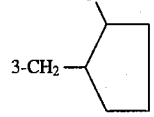

| Compound No. | R | X | Y | Z | Melting point (°C.) or Refractive index ($n^{20}_D$) |
|---|---|---|---|---|---|
| 176 | 3-CH$_2$-(2-methylcyclopentyl) | H | $C_3H_7$-i | N | 1.5450 |
| 177 | 3-CH$_2$-(2-methylcyclopentyl) | H | $C_3H_7$ | N | 1.5477 |
| 178 | 3-O-(2-methyl-4-methylcyclohexyl) | H | $C_3H_7$-i | N | 1.5428 |
| 179 | 5-CH$_2$OC(CF$_3$)$_3$ | 2-F | $C_3H_7$ | N | 1.4778 |
| 180 | 3-CH$_2$-cyclohexyl | H | $C_3H_7$ | N | 1.5478 |
| 181 | 5-CH$_2$-cyclohexyl | 2-F | $C_3H_7$-i | N | 1.5345 |
| 182 | 3-CH$_2$OC(CF$_3$)$_3$ | 4-F | $C_3H_7$-i | N | 1.4772 |
| 183 | 3-CH$_2$OC(CF$_3$)$_3$ | 4-F | $C_3H_7$ | N | 1.4788 |
| 184 | 3-C$_2$H$_4$Si(CH$_3$)$_3$ | H | $C_3H_7$ | N | 1.5289 |
| 185 | 3-C$_2$H$_4$Si(CH$_3$)$_3$ | H | $C_3H_7$-i | N | 1.5272 |

The compounds according to the present invention can be produced by the following Methods A to D.

Method A
(Scheme 1)

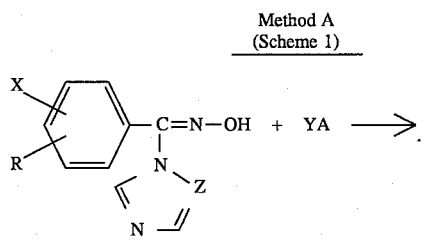 + YA ⟶ 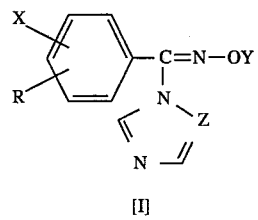

[II]   [III]   [I]

wherein A is a halogen atom; and R, X, Y, and Z are the same as described above.

The compound represented by formula [I] can be produced by the reaction between the benzohydroximoylazole compound represented by formula [II] and the halogen compound represented by formula [III] in the presence of a base. In this reaction, the halogen compound or sulfonic ester compound may be employed in the amount of one or more equivalents. In addition, the base employed in the reaction includes an inorganic base, for example, an alkali metal hydroxide such as sodium hydroxide, potassium hydroxide, or the like; an alkali metal carbonate such as sodium carbonate, potassium carbonate, or the like; an alkali metal bicarbonate such as sodium bicarbonate, potassium bicarbonate, or the like, or an organic base such as triethylamine, N,N-dimethylaniline, pyridine, 1,8-diazacyclo[5,4,0]unde-7-cene, or the like.

The reaction can be carried out in the presence of a diluent, if necessary. The diluent includes water or inactive organic solvent. For example, a ketone such as acetone, butanone, or the like; an aromatic hydrocarbon which may be halogenated such as benzene, toluene, xylene, chlorobenzene, or the like; an aliphatic hydrocarbon such as petrolem ether, ligroin, or the like; an ether such as diethyl ether, tetrahydrofuran, dioxane, or the like; a nitrile such as acetonitrile, propionitrile, or the like; or an amide such as N,N-dimethylformamide, N,N-dimethylacetamide, N-methylpyrrolidone, or the like may be employed.

The synthesizing reaction temperature is set in the range of 0° C. to the reflux temperature of the reaction system, preferably in the range of 40° C. to 100° C. The reaction time depends on type of compound. The reaction may be usually completed for 1 hour to 6 hours.

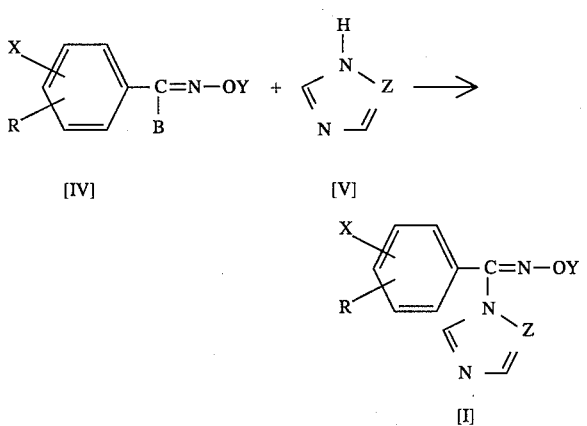

wherein B is a halogen atom, R, X, Y, and Z are the same as described above.

The compound represented by formula [I] can be produced by the reaction between the benzohydroximoylhalide compound represented by formula [IV] and the azole or triazole compound represented by formula [V] in the presence of a base. In this reaction, the azole or triazole compound can be employed in the amount of one or more equivalents with the base or the solvent. In addition, the same base as described in Method A can be employed.

The reaction can be carried out in the presence of an adequate dilute, if necessary. The same dilute as described above can be employed.

The synthesizing reaction temperature is set in the range of room temperature to the reflux temperature, preferably in the range of 80° C. to 130° C. The reaction time depends on type of compound. The reaction may be usually completed in 2 hours to 5 hours in a good yield.

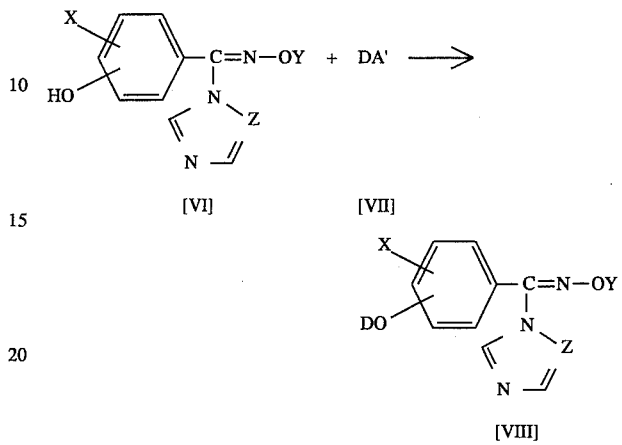

wherein D is a branched alkyl group having not fewer than 3 carbon atoms, a halogen-substituted alkyl group having not fewer than 3 carbon atoms, a substituted silylalkyl group, a cycloalkyl group which may be substituted with one or two alkyl groups, or a halogen-substituted alkenyl group; A' is a halogen atom, an alkylsulfonyloxy group, a benzenesulfonyloxy group which may be substituted, and X, Y, and Z are the same as described above.

The compound represented by formula [VIII] can be produced by the reaction between the compound having a hydroxide group on the benzene ring represented by formula [VI] and the halogen compound or sulfonate (ester) compound represented by formula [VII] in the presence of a base. In this reaction, the halogen compound or sulfonate (ester) compound can be employed in the amount of one or more equivalents. In addition, the same base as described in Method A can be employed.

The reaction can be carried out in the presence of an adequate dilute, if necessary. The same dilute as described above can be employed.

The synthesizing reaction temperature is set in the range of 0° C. to the reflux temperature of the reaction system, preferably in the range of 40° C. to 120° C. The reaction time depends on type of compound. The reaction may be usually completed in 1 hour to 8 hours.

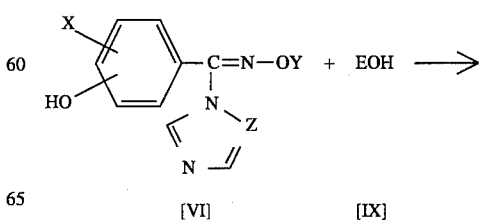

-continued
Method D
(Scheme 4)

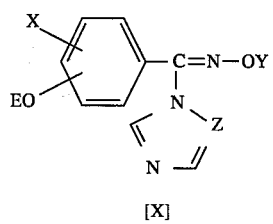

[X]

wherein E is a branched alkyl group having not fewer than 3 carbon atoms, a fluorine-substituted alkyl group having not fewer than 3 carbon atoms, a substituted silylalkyl group, a cycloalkyl group which may be substituted with one or two alkyl groups, or a halogen-substituted alkenyl group; X, Y, and Z are the same as described above.

The compound represented by formula [X] can be produced by a reaction between the compound having a hydroxide group on the benzene ring represented by formula [VI] and an alcoholic compound represented by formula [IX] in the presence of triphenylphosphine and diethyl azodicarboxylate or dimethyl azocarboxylate. In this reaction, the alcoholic compound can be employed in the amount of one or more equivalents.

The reaction can be carried out in the presence of an adequate dilute, if necessary. In addition, the same dilute as described in Method A can be employed. Preferably, acetonitrile or tetrahydrofuran is adequate.

The synthesizing reaction temperature is set in the range of 0° C. to the reflux temperature, preferably in the range of 30° C. to 120° C. The reaction time depends on type of compound. The reaction may be usually completed in 0.5 hours no 72 hours.

PREFERRED EMBODIMENTS OF THE INVENTION

The methods for producing the compounds according to the present invention will be concretely described in examples.

EXAMPLE 1

Synthesis of 1-[O-isopropyl-3-(3,3-dimethylbutoxy) benzohydroximoyl]-1H-1,2,4-triazole (Compound 19)

To a solution of 1.6 g (5.6 mmol) of 1-[3-3,3-dimethylbutoxy) benzohydroximoyl] -1H-1,2,4-triazole dissolved in 100 ml of N,N-dimethylformamide was added 0.16 g (6.7 mmol) of sodium hydride. The mixture was stirred for 20 minutes at 80° C., and then allowed to sit and cool naturally to about 50° C. To the mixture was added 1.1 g (6.5 mmol) of 2-iodopropane and stirred for 1 hour at about 50° C. The reaction mixture was allowed to sit and cool naturally to room temperature. The cooled mixture was poured into water and extracted with ethyl acetate. After being washed with water, the organic layer was dried over anhydrous magnesium sulfate. The solvent in the organic layer was removed under reduced pressure. The residue was purified by column chromatography, thus obtaining 1.4g (yield: 87%) of the desired product having a refractive index of $[n_D^{20}]$ 1.5289 at 20° C.

EXAMPLE 2

Synthesis of 1-(O-isopropyl-3-isopentylbenzohydroxymoyl)-1H-1,2,4-triazole (Compound 9)

To 100 ml of N,N-dimethylformamide was added 1.5 g (5.6 mmol) of O-isopropyl-3-isopentylbenzohydroximoyl chloride, 0.8 g (11.6 mmol) of 1,2,4-triazole, and 1.6 g (11.6 mmol) of potassium carbonate. The mixture was stirred at 120° C. for 3 hours to complete the reaction. The reaction mixture was allowed to sit and cool naturally to room temperature. The cooled reaction mixture was poured into water and extracted with ethyl acetate. After being washed with water, the organic layer was dried over anhydrous magnesium sulfate. The solvent in the organic layer was then removed under reduced pressure. The residue was purified by column chromatography, thus obtaining 1.2 g (yield: 71%) of the desired product having a refractive index of $[n_D^{20}]$ 1.5317 at 20° C.

EXAMPLE 3

Synthesis or 1-(O-isopropyl-3-isobutoxybenzohydroxymoyl)-1H-1,2,4-triazole (Compound 3)

To 100 ml of N,N-dimethylformamide was added 1.2 g (4.9 mmol) of 1-(O-isopropyl-3-hydroxybenzohydroximoyl) -1H- 1,2,4-triazole, 0.7 g (5.1 mmol) of isobutyl bromide, and 0.8 g (5.8 mmol) of potassium carbonate. The mixture was stirred for 1 hour at 80° C. to complete the reaction. The reaction mixture was allowed to sit and cool naturally. The cooled reaction mixture was poured into water and extracted with ethyl acetate. The organic layer was dried over anhydrous magnesium sulfate. The solvent in the organic layer was then removed under reduced pressure. The residue was purified by column chromatography, thus obtaining 1.1 g (yield: 73%) of the desired product having a refractive index of $[n_D^{20}]$ 1.5341 at 20° C.

EXAMPLE 4

Synthesis or 1-(O-isopropyl-3-neopentyloxybenzohydroxymoyl)-1H-1,2,4-triazole (Compound 44)

2.5 g (0.010M) of 1-(O-isopropyl-3-hydroxybenzohydroximoyl)- 1H-1,2,4-triazole of, 0.9 g (10.0 mmol) of 2,2-dimethyl-1-propanol, and 2.6 g (10.0 mmol) triphenylphosphine were dissolved in 40 ml of tetrahydrofuran. The solution was cooled to not more than 10° C. in a water bath. To the solution was added 1.7 g (10.0 mmol) of diethyl azodicarboxylate drop by drop so that the temperature of the solution was not over 20° C. The mixture was stirred overnight, and then heated to 60° C. The reaction mixture was then concentrated. The residue was purified by column chromatography, thus obtaining 0.8 g (yield: 25%) of the desired product having a refractive index of $[n_D^{20}]$ 1.5202 at 20° C.

EXAMPLE 5

Synthesis of 1-(O-ethyl-3-trimethylsilylmethoxybenzohydroxymoyl)-1H-1,2,4-triazole (Compound 147)

1.5 g of 1-(3-trimethylsilylmethoxybenzohydroximoyl)-1H-1,2,4-triazole was dissolved in a mixed solvent of 50 ml of dried tetrahydrofuran (THF) and 50 ml of dimethylformamide (DMF). To the solution was added 0.15 g of sodium hydride, and the mixture was stirred for 10 minutes at room temperature. Ten ml of a THF solution dissolving 2.0 g of ethyl iodide was dropped into the mixture for 15 minutes. The reaction mixture was then stirred for 3 hours at 50° C. to complete the reaction. The resultant mixture was condensed in the half volume under reduced pressure. After the condensed mixture was allowed to sit and cool, it was poured into a large amount of water. The organic layer was extracted with ethyl acetate and dried over magnesium sulfate. The solvent of the organic layer was removed under reduced pressure. The residue was purified by column chromatography (eluate: hexane/ethyl acetate= 4/1), thus obtaining 1.2 g (yield: 75%) of the desired product of having a refractive index of $[n_D^{20}]$ 1.5385 at 20° C.

EXAMPLE 6

Synthesis of 1-(O-isopropyl-3-cyclohexylbenzohydroxymoyl)-1H-1,2,4-triazole (Compound 153)

3.3 g of O-isopropyl-3-cyclohexylbenzohydroxymoyl chloride, 1.6 g of 1,2,4-triazole, and 3.3 g of potassium carbonate were dissolved in 100 ml of N,N-dimethylacetamide (DMAC). The mixture was stirred for 2 hours at 130° C. After the reaction mixture was allowed to sit and cool naturally, it was poured into water. The organic layer was extracted with ethyl acetate and dried over magnesium sulfate. The solvent in the organic layer was removed under reduced pressure. The residue was purified by column chromatography (eluate: hexane/ethyl acetate= 4/1), thus obtaining 3.1 g (yield: 84%) of the desired product (white solid) of having a melting point of 49° C.~51° C.

EXAMPLE 7

Synthesis of 1-[O-isopropyl-{3-(1,1,1,3,3,3-hexafluoro-2-methyl-2-propoxy)methyl} benzohydroximoyl]-1H- 1,2,4-triazole (Compound 162)

1.2 g of O-isopropyl-{3-(1,1,1,3,3,3-hexafluoro-2-methyl- 2-propoxy)methyl}benzohydroximoyl chloride, 0.4 g of 1,2,4-triazole, and 0.9 g of potassium carbonate were added to 50 ml of DMAC. The mixture was stirred at for 3 hours 130° C. After the resultant mixture was allowed to sit and cool naturally, it was poured into water. The organic layer was extracted with ethyl acetate and dried over magnesium sulfate. The solvent in the organic layer was removed under reduced pressure. The residue was purified by column chromatography (eluate: hexane/ethyl acetate= 4/1), thus obtaining 0.9 g (yield: 69%) of the desired product (transparent viscous liquid) having a refractive index of $[n_D^{20}]$ 1.4821 at 20° C.

EXAMPLE 8

Synthesis of 1-(O-isopropyl-3-trimethylsilylmethoxy-benzohydroximoyl)- 1H-1,2,4-triazole (Compound 140)

2.7 g of 1-(O-isopropyl-3-hydroxybenzohydroximoyl)-1H- 1,2,4-triazole, 1.5 g of chlorotrimethylsilane, 1.8 g of potassium carbonate, and a small amount of potassium iodide catalyst were added to 100 ml of DMF. The mixture was stirred for at 90° C. 2 hours. After the resultant mixture was allowed to sit and cool naturally, it was poured into water. The organic layer was extracted with ethyl acetate and dried over magnesium sulfate. The solvent in the organic layer was removed under reduced pressure. The residue was purified by column chromatography (eluate: hexane/ethyl acetate= 4/1), thus yielding 3.2 g (yield: 89%) of the desired product (transparent viscous liquid) having a refractive index of $[n^{20}]$ 1.5310 at 20° C.

EXAMPLE 9

Synthesis of 1-(O-isopropyl-3-cyclohexyloxybenzohydroxymoyl)- 1H-1,2,4-triazole (Compound 158)

2.0 g of 1-(O-isopropyl-3-hydroxybenzohydroximoyl) -1H- 1,2,4-triazole, 1.6 g of cyclohexanol, and 4.3 g of triphenylphosphine were dissolved in 100 ml of THF. The mixture was maintained at about 5° C. To the solution was added 10 ml of a THF solution dissolving 2.8 g of diethyl azodicarboxylate drop by drop for 30 minutes. The mixture was stirred for 8 hours at room temperature. The solvent in the resultant mixture was removed under reduced pressure. The residue was purified by column chromatography (eluate: hexane/ethyl acetate= 4/1), thus obtaining 2.1 g (yield: 78%) of the desired product (transparent viscous liquid) having a refractive index of $[n_D^{20}]$ 1.5490 at 20° C.

The compounds represented by formula [II], [IV], and [VI], which are raw materials of the compounds according to the present invention, can be produced in the Methods a to c.

Method a
(Scheme 5)

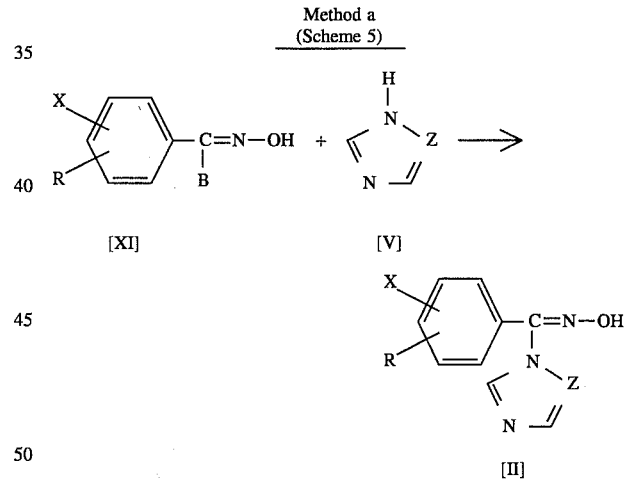

wherein R, X, Z, and B are the same as described above.

The benzohydroximoylazole compound represented by formula [II] can be synthesized by a reaction between a benzohydroximoylhalide compound represented by formula [XI] and an azole or triazole compound represented by the formula [V], for example, in a solvent such as acetonitrile or the like in the presence of a base such as potassium carbonate or the like.

The synthesizing reaction temperature is set in the range of 0° C. to the reflux temperature of the reaction system, preferably 50° C. to 80° C. The reaction time depends on type of the compound. The reaction will usually be completed in 1 hour to 6 hours.

Method b
(Scheme 6)

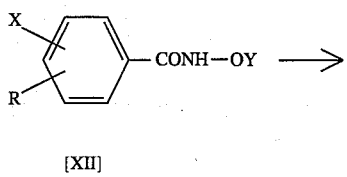

[XII]

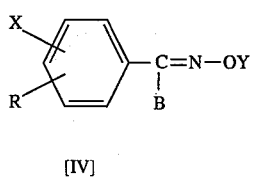

[IV]

wherein R, X, Z, and B are the same as described above.

The benzohydroximoylhalide compound represented by formula [IV] can be synthesized by reacting the benzamide compound represented by formula [XII] with the halogenation reagent such as phosphorus pentachloride, thionyl chloride, or the like in the presence or absence of an inactive solvent of an aromatic hydrocarbon such as benzene, toluene, or the like; a halogenated hydrocarbon such as chloroform, carbon tetrachloride, or the like. In addition, the benzohydroximoylhalide compound represented by formula [IV] can also be synthesized by reacting the benzamide compound represented by formula [XII] with the halogenation reagent comprising triphenyl phosphine and carbon tetrachloride, or triphenyl phosphine and carbon tetrabromide in the presence of an inactive solvent of a nitrile such as acetonitrile, propionitrile, or the like, or an aromatic hydrocarbon such as benzene, chlorobenzene, or the like. In this case, carbon tetrachloride and carbon tetrabromide can be employed as the solvent.

The synthesizing reaction temperature is set in the range of 0° C. to the reflux temperature of the reaction system, preferably 50° C. to 80° C. The reaction time depends on the type of compound. The reaction may be usually completed in 1 hour to 6 hours.

Method c
(Scheme 7)

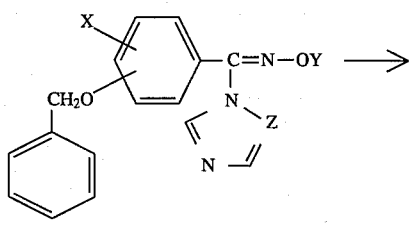

[XIII]

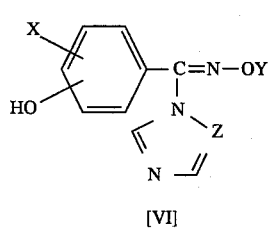

[VI]

wherein X, Y, and Z are the same as described above.

The compound represented by formula [VI] can be synthesized by hydrocracking the corresponding benzyloxy compound represented by formula [XIII] in the presence of a catalyst of carbon palladium in an inactive solvent of aprotic polar solvent, for example, water, acetic acid, an alcohol, an ethyl acetate, N,N-dimethylacetamide, N,N-dimethylformamide, or the like. In addition, the compound represented by formula [VI] can be also synthesized by debenzylating the corresponding benzyloxy compound represented by formula [XIII] using boron tribromide or boron trichloride in an inactive solvent of an aromatic hydrocarbon such as benzene, chlorobenzene, or the like, or a halogenated hydrocarbon such as dichloromethane, 1,2-dichloroethane, or the like.

The synthesizing reaction temperature is set in the range of −60° C. to 40° C., preferably −30° C. to room temperature. The reaction time depends on the type of compound. The reaction may be usually completed in 1 hour to 8 hours.

Furthermore, the compounds represented by formulae [XI], [XII], and [XIII] can be produced by the following methods:

The compound represented by formula [XI] can be synthesized by reacting the corresponding benzaldoxime, obtained by a reaction between the corresponding benzaldehyde compound and hydroxylamine hydrochloride using a known method, with a halogenation reagent such as N-bromosuccinimide, N-chlorosuccinimide, chlorine, or the like.

The compound represented by formula [XII] can be synthesized by reacting benzoylhalide or N-imidazylimidazole imidazylimidazole derived from the corresponding benzoic acid derivative with alkoxyamine.

In addition, the benzyloxy compound represented by formula [XIII] can be synthesized by the following successive steps of benzylating the hydroxy benzoic acid derivative; synthesizing halide benzoate from the benzylated compound in the known method; reacting the halide benzoate with alkoxyamine; halogenating it according to Method b; and carrying out the steps in Method B.

Examples

Next, the method for producing the raw materials according to the present invention will be described in detail with reference to the following examples.

EXAMPLE 10

Synthesis of 1-[3-(3,3-dimethylbutoxy) benzohydroximoyl]-1H-1,2,4-triazole

To 100 ml of 1,2-dimethoxyethane were added 2.0 g (7.8 mmol) of 3-(3,3-dimethylbutoxy)benzohydroximoyl chloride, 1.9 g (27.5 mmol) of 1,2,4-triazole, and 1.5 g (10.9 mmol) of potassium carbonate. The mixture was stirred for 8 hours at about 50° C. After the resultant mixture was allowed to sit and cool naturally, the solvent in the mixture was removed. The residue was purified by column chromatography, thus obtaining the desired product of 1.2 g (yield: 46%).

EXAMPLE 11

Synthesis of O-isopropyl-3-isopentylbenzohydroximoyl chloride

To 200 ml of acetonitrile were added 5.4 g (23.5 mmol) of O-isopropyl 3-isopentylbenzohydroxamic acid, 9.9 g (37.8 mmol) of triphenylphosphine, and 11.6 g (75.3 mmol) of carbon tetrachloride. The mixture was refluxed for 1 hour.

The refluxed mixture was allowed to sit and cool naturally, and the solvent in the mixture was removed under reduced pressure. The residue was purified by column chromatography, thus obtaining the desired product of 5.1 g (yield: 88%).

EXAMPLE 12

Synthesis of 1-(O-isopropyl-3-hydroxybenzohydroximoyl)-1H-1,2,4-triazole

To 150 ml of ethyl acetate were added 5.0 g of 1-(O-isopropyl- 3-benzyloxybenzohydroximoyl)-1H-1,2,4-triazole (melting point: 62° C. to 67° C.) and 1 g of 10% palladium carbon at room temperature. In connection with the mixture, the hydrogenolysis reaction was carried out. After 8 hours, the palladium carbon was removed. The filtrate was then concentrated. The residue was purified by column chromatography, thus yielding 3.2 g (yield: 89%) of the desired product having a melting point of 160° C. to 163° C.

The insecticide according to the present invention includes the benzohydroximoylazole derivative represented by formula [I] as an active ingredient.

In the case where the compounds according to the present invention are employed as an insecticide, the compounds can be used alone or in combination with carriers, surfactants, dispersants, auxiliary agents, or the like, which are needed for formulation, and then formulated in a known manner, for example, into a dust, a wettable powder, an emulsifiable concentrate, fine particles, granules, or the like.

Suitable examples of carriers employed in the formulation are solid carriers such as zirclite, talc, bentonite, clay, kaolin, diatomaceous earth, white carbon, vermiculite, slaked lime, siliceous sand, ammonium sulfate, and urea; and liquid carriers such as isopropyl alcohol, xylene, cyclohexanone, methylnaphthalene, and the like. Illustrative examples of the surfactants and dispersants include metal salts of alkylbenzenesulfonic acid and dinaphthylmethanedisulfonic acid, salts of alcohol sulfuric acid esters, alkylarylsulfonic acid salts, ligninesulfonic acid salts, polyoxyethylene glycol ethers, polyoxyethylene alkyl aryl ethers, polyoxyethylenesorbitan monoalkylates, and the like.

Suitable examples of auxiliary agents include carboxymethylcellulose, polyethylene glycol, gum arabic, and the like.

These preparations can be applied directly, or after diluting the preparation to a suitable concentration.

The proportion of the active ingredient is selected as needed. When formulated into a dust or granules, 0.05% by weight to 20% by weight (preferably 0.1% by weight to 10% by weight) of the active ingredient is preferred. For an emulsifiable concentrate or wettable powder, 0.5% by weight to 80% by weight (preferably 1% by weight to 80% by weight) of the active ingredient is adequate.

The insecticide according to the present invention can be used for a number of purposes. For example, spraying of stem and leaf portions, injection into the irrigation water, and injection into the soil prior to seeding, at the time of seeding, at the time of transplantation, and during the maturation of the plant. The insecticide of the present invention also has fungicidal properties.

The rate of application of the insecticide according to the present invention may vary depending on the type of the active compound employed, the kind of the pest or disease to be controlled, the nature of occurrence of the pest or disease, the degree of damage, environmental conditions, the preparation form to be used, and the like.

When the insecticide of the present invention is applied directly in the form of dust or granules, it is recommended that the rate of application of the active ingredient be suitably chosen in the range of 0.05 g and 5 kg per 10 acres, preferably, in the range of 0.1 g and 1 kg per 10 acres. In addition, when the insecticide of the present invention is in the form of liquid such as an emulsifiable concentrate or a wettable powder, it is recommended that the rate of application of the active ingredient be suitably chosen in the range of 0.1 ppm and 5000 ppm, and preferably in the range of 1 ppm and 1000 ppm.

The insecticide according to the present invention can be employed alone or in combination with other insecticides or fungicides.

Next, the representative formulations are illustrated with reference to the following Formulation Examples, wherein all designations of "%" are given in "percent by weight". The kind and proportion of compounds and auxiliary agents are not restricted as described in the following examples.

Formulation Example 1: Emulsifiable Concentrate

Thirty % of Compound (9), 20% of cyclohexanone, 11% of polyoxyethylene alkylaryl ether, 4% of calcium alkylbenzenesulfonate, and 35% of methylnaphthalene were uniformly dissolved, thus obtaining an emulsifiable concentrate.

Formulation Example 2: Wettable Powder

Fourty % of Compound (10), 15% of diatomaceous earth, 15% of clay, 25% of white carbon, 2% of sodium dinaphtylmethanesulfonate, and 3% of sodium ligninsulfonate were uniformly mixed and ground into a wettable powder.

Formulation Example 3: Dust

Two % of Compound (17), 5% of diatomaceous earth, and 93% of clay were uniformly mixed and ground into a dust.

Formulation Example 4: Granules

Five % of Compound (1), 2% of sodium salt of the ester of lauryl alcohol, 5% of sodium ligninsulfonate, 2% of carboxymethylcellulose, and 86% of clay were mixed and ground. One hundred parts by weight of the ground mixture was added to 20 parts by weight of water. The resulting mixture was kneaded and formed into granules of 14 mesh to 32 mesh by means of an extrusion granulator. The formed granules were then dried into the desired granules.

EFFECT OF THE INVENTION

The benzohydroximoylazole derivatives according to the present invention exhibit an improved control of harmful hemipterans such as Delphacidae including *Nilaparavata lugens, Sogatella furcifera, Laodelphax striatellus* or the like, Deltocephalidae including *Nephotettix cincticeps, Empoasca onukii* or the like, Aphididae including *Aphis gossypii, Myzus persicae, Brevicoryne brassicae* or the like, Alevrodidae including *Trialeurodes vaporariorum* or the like, Pseudococcidae including *Pseudococcus comstocki* or the like, Pentatomidae including *Leptocorixa corbetti* or the like, in comparison with the compounds described in Japanese Patent Application First Publication No. 1-308260. In addition, the benzohydroximoylazole derivatives according to the present invention are effective to the harmful insects such as Lepidoptera including *Plutella xylostella, Spodopnera litura,* or the like, Diptera including *Musca domestica,* or the like, Coleopteraa including *Lissorhoptrus oryzophilus, Callosobruchus chinesis, Aulacophora femoralis* or the like, Orthoptera including *Blattella germanica,* or the like, Tetranychidae including *Tetranychus urticae, Panonychus citri,* or the like, Furthermore, the compounds of the present invention exhibit fungicidal activities and are able to effectively control the pathogens which cause rice blast (*Pyricularia oryzae*), rice sheath blight (*Rhizoctonia solani*), cucumber downy mildew (*Pseudoperonospra cubensis*), cucumber gray mold (*Botrytis cinerea*), cucumber powdery mildew (*Sphaerotheca fuliginea*), *Pseudomonas lachrymans,* and Alternaria sooty spot of Chinese mustard (*Altternaria brassicicola*).

The effects of the compounds according to the present invention are now illustrated with reference to the following Test Examples.

Test Example 1

Mortality test of *Neophotettix cincticeps* exhibiting pesticide resistance to the commercially available reagents The wettable powder prepared according to Formulation Example 2 was diluted with water to the concentration of 20 ppm. into the aqueous preparation obtained, the stems and leaves of rice plants were dipped. After being air-dried, the stems and leaves were allowed to stand in a test tube. The 10 larvae of *Neophotettix cincticeps* were then added into the test tube, and the opening of the test tube was closed by absorbent cotton. After the closed test tube was placed in a thermostatic chamber at 25° C. for 6 days, the number of dead insects was counted and the percentage of dead insects was calculated. The results are shown in Table 2.

The test was then repeated. As comparative reagents, the compounds listed below, which are disclosed in Japanese Patent Application First Publication No. 1-308260, phenobcarb, and malathion were employed. The comparative tests were carried out in the concentration of 1000 ppm of the commercially available reagents.
Comparative compound 1:
  1-(O-ethyl-4-butylbenzohydroximoyl)-1H-1,2,4-triazole
Comparative compound 2:
  1-(O-isopropyl-4-butylbenzohydroximoyl)-1H-1,2,4-triazole
Comparative compound 3:
  1-(O-isopropyl-4-butylbenzohydroximoyl)-1H-1,2,4-triazole
Comparative compound 4:
  1-(O-isopropyl-4-hexylbenzohydroximoyl)-1H-1,2,4-triazole
Comparative compound 5:
  1-(O-propyl-3-(2,2,2-trifluoroethoxybenzohydroximoyl)-1H-1,2,4-triazole
Comparative compound 6:
  1-(O-isopropyl-2-chloro-5-methoxybenzohydroximoyl)-1H-1,2,4-triazole
Comparative compound 7:
  Phenobcarb (common name, produced by Kumiai Chemical Industries, Co., Ltd.)
Comparative compound 8:
  Malathion (common name, produced by Kumiai Chemical Industries, Co., Ltd.)

TABLE 2

| Compound No. | Dead Insects (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 100 |
| 72 | 100 |
| 73 | 100 |
| 74 | 100 |
| 75 | 100 |

TABLE 2-continued

| Compound No. | Dead Insects (%) |
|---|---|
| 76 | 100 |
| 77 | 100 |
| 78 | 100 |
| 79 | 100 |
| 80 | 100 |
| 81 | 100 |
| 82 | 100 |
| 83 | 100 |
| 84 | 100 |
| 85 | 100 |
| 86 | 100 |
| 87 | 100 |
| 88 | 100 |
| 89 | 100 |
| 90 | 100 |
| 115 | 100 |
| 116 | 100 |
| 117 | 100 |
| 118 | 100 |
| 119 | 100 |
| 120 | 100 |
| 121 | 100 |
| 122 | 100 |
| 123 | 100 |
| 124 | 100 |
| 125 | 100 |
| Comparative compound 1 | 30 |
| Comparative compound 2 | 60 |
| Comparative compound 3 | 50 |
| Comparative compound 4 | 40 |
| Comparative compound 5 | 30 |
| Comparative compound 6 | 20 |
| Comparative compound 7 (Commercially available reagent) | 30 |
| Comparative compound 8 (Commercially available reagent) | 40 |

Test Example 2

Mortality test or *Nilaparavata lugens*

The wettable powder prepared according to Formulation Example 2 was diluted with water to the predetermined concentration. Into the aqueous preparation obtained, the stems and leaves of the rice plant were dipped. After being air-dried, the stems and leaves were allowed to stand in a test tube. The 10 larvae of *Nilaparavata lugens* were added into the test tube, and the opening of the test tube was closed by the absorbent cotton. After the closed test tube was placed in a thermostatic chamber at 25° C. for 6 days, the number of dead insects was counted and the percentage of dead insects was calculated. The results are shown in Table 3.

The same comparative compounds as described in Test Example 1 were employed.

TABLE 3

| Compound No. | Dead Insects (%) | |
|---|---|---|
| | 20 ppm | 4 ppm |
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 100 |
| 15 | 100 | 100 |
| 16 | 100 | 100 |
| 17 | 100 | 100 |
| 18 | 100 | 100 |
| 19 | 100 | 100 |
| 20 | 100 | 100 |
| 21 | 100 | 100 |
| 22 | 100 | 100 |
| 23 | 100 | 100 |
| 24 | 100 | 100 |
| 25 | 100 | 100 |
| 26 | 100 | 100 |
| 27 | 100 | 100 |
| 28 | 100 | 100 |
| 29 | 100 | 100 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66 | 100 | 100 |
| 67 | 100 | 100 |
| 68 | 100 | 100 |
| 69 | 100 | 100 |
| 70 | 100 | 100 |
| 71 | 100 | 100 |
| 72 | 100 | 100 |
| 73 | 100 | 100 |
| 74 | 100 | 100 |
| 75 | 100 | 100 |
| 76 | 100 | 100 |
| 77 | 100 | 100 |
| 78 | 100 | 100 |
| 79 | 100 | 100 |
| 80 | 100 | 100 |
| 81 | 100 | 100 |
| 82 | 100 | 100 |
| 83 | 100 | 100 |
| 84 | 100 | 100 |
| 85 | 100 | 100 |
| 86 | 100 | 100 |

TABLE 3-continued

| Compound No. | Dead Insects (%) | |
| --- | --- | --- |
| | 20 ppm | 4 ppm |
| 87 | 100 | 100 |
| 88 | 100 | 100 |
| 89 | 100 | 100 |
| 90 | 100 | 100 |
| 91 | 100 | 100 |
| 115 | 100 | 100 |
| 117 | 100 | 100 |
| 118 | 100 | 100 |
| 119 | 100 | 100 |
| 120 | 100 | 100 |
| 121 | 100 | 100 |
| 122 | 100 | 100 |
| Comparative compound 1 | 90 | 50 |
| Comparative compound 2 | 90 | 70 |
| Comparative compound 3 | 90 | 70 |
| Comparative compound 4 | 60 | 30 |
| Comparative compound 5 | 90 | 50 |
| Comparative compound 6 | 100 | 70 |

Test Example 3

Mortality test of *Aphis gossypii*

The wettable powder prepared according to Formulation Example 2 was diluted with water to the concentration of 100 ppm. Into the aqueous preparation obtained, seedlings of the cucumber plane were dipped. After being air-dried, they were allowed to stand in a polyethylene cup having a diameter of 55 mm. Ten larvae of *Aphis gossypii* were put on the leaves of the seedlings in the cup. After the cup was placed in a thermostatic chamber at 25° C. for 3 days, the number of dead insects was numbered and the percentage of dead insects was calculated. The test was then repeated. The results are shown in Table 4.

TABLE 4

| Compound No. | Dead Insects (%) |
| --- | --- |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| 81 | 100 |
| 82 | 100 |
| 83 | 100 |
| 84 | 100 |
| 85 | 100 |
| 86 | 100 |
| 87 | 100 |
| 88 | 100 |
| 89 | 100 |
| 90 | 100 |
| 91 | 100 |
| 115 | 100 |
| 117 | 100 |
| 118 | 100 |
| 119 | 100 |

Test Example 4

Mortality test of *Nilapara lugens*

The wettable powder prepared according to Formulation Example 2 was diluted with water to the predetermined concentration. Into the aqueous preparation obtained, the seems and leaves of rice plants were dipped. After being air-dried, the stems and leaves were allowed to stand in a test tube. Ten larvae of *Nilapara lugens* were added into the test tube, and the opening of the test tube was closed by absorbent cotton. After the closed test tube was placed in a thermostatic chamber at 25° C. for 6 days, the number of dead insects was counted and the percentage of dead insects was calculated. The test was then repeated. The results are shown in Table 5.

TABLE 5

| Compound No. | Dead Insects (%) | |
| --- | --- | --- |
|  | 20 ppm | 4 ppm |
| 140 | 100 | 100 |
| 141 | 100 | 100 |
| 142 | 100 | 100 |
| 143 | 100 | 100 |
| 144 | 100 | 100 |
| 145 | 100 | 100 |
| 146 | 100 | 100 |
| 147 | 100 | 100 |
| 148 | 100 | 100 |
| 149 | 100 | 100 |
| 150 | 100 | 100 |
| 151 | 100 | 100 |
| 152 | 100 | 100 |
| 153 | 100 | 100 |
| 154 | 100 | 100 |
| 155 | 100 | 100 |
| 156 | 100 | 100 |
| 157 | 100 | 100 |
| 158 | 100 | 100 |
| 159 | 100 | 100 |
| 160 | 100 | 100 |
| 161 | 100 | 100 |
| 162 | 100 | 100 |
| 163 | 100 | 100 |
| 164 | 100 | 100 |
| 165 | 100 | 100 |
| 166 | 100 | 100 |
| 167 | 100 | 100 |
| 168 | 100 | 100 |
| 169 | 100 | 100 |
| 170 | 100 | 100 |
| 171 | 100 | 100 |
| 172 | 100 | 100 |
| 173 | 100 | 100 |
| 174 | 100 | 100 |
| 175 | 100 | 100 |
| 176 | 100 | 100 |
| 177 | 100 | 100 |
| 178 | 100 | 100 |
| 179 | 100 | 100 |
| 180 | 100 | 100 |
| 181 | 100 | 100 |
| 182 | 100 | 100 |
| 183 | 100 | 100 |
| 184 | 100 | 100 |
| 185 | 100 | 100 |

Test Example 5

Mortality test of *Nephotettix cincticeps* exhibiting pesticide resistance to the commercially available reagents The wettable powder prepared according to Formulation Example 7 was diluted with water to the concentration of 100 ppm. Into the aqueous preparation obtained, the stems and leaves of rice plants were dipped. After being air-dried, the stems and leaves were allowed to stand in a test tube. Five larvae of *Nephotettix cincticeps* were added into the test tube, and the opening of the test tube was closed by absorbent cotton. After the closed test tube was placed in a thermostatic chamber at 25° C. for 6 days, the dead insects were counted and the percentage of dead insects was calculated. The test was then repeated. The results are shown in Table 6.

TABLE 6

| Compound No. | Dead Insects (%) |
| --- | --- |
| 140 | 100 |
| 141 | 100 |
| 142 | 100 |
| 143 | 100 |
| 144 | 100 |
| 145 | 100 |
| 146 | 100 |
| 147 | 100 |
| 148 | 100 |
| 149 | 100 |
| 150 | 100 |
| 151 | 100 |
| 152 | 100 |
| 153 | 100 |
| 154 | 100 |
| 155 | 100 |
| 156 | 100 |
| 157 | 100 |
| 158 | 100 |
| 159 | 100 |
| 160 | 100 |
| 161 | 100 |
| 162 | 100 |
| 163 | 100 |
| 164 | 100 |
| 165 | 100 |
| 166 | 100 |
| 167 | 100 |
| 168 | 100 |
| 169 | 100 |
| 170 | 100 |
| 171 | 100 |
| 172 | 100 |
| 173 | 100 |
| 174 | 100 |
| 175 | 100 |
| 176 | 100 |
| 177 | 100 |
| 178 | 100 |
| 179 | 100 |
| 180 | 100 |
| 181 | 100 |
| 182 | 100 |
| 183 | 100 |
| 184 | 100 |
| 185 | 100 |

Test Example 6

Mortality test of *Aphis gossypii*

The wettable powder prepared according to Formulation Example 2 was diluted with water to the concentration of 100 ppm. Into the aqueous preparation obtained, seedlings of the cucumber plant were dipped. After being air-dried, they were allowed to stand in a polyethylene cup having a diameter of 55 mm. Ten larvae of *Aphis gossypii* were put on the leaves of the cucumber plant. After the cup was placed in a thermostatic chamber at 25° C. for 3 days, the dead insects were counted and the percentage of dead insects was calculated. The test was then repeated. The results are shown in Table 7.

TABLE 7

| Compound No. | Dead Insects (%) |
| --- | --- |
| 140 | 100 |
| 141 | 100 |
| 142 | 100 |
| 143 | 100 |
| 144 | 100 |
| 145 | 100 |

TABLE 7-continued

| Compound No. | Dead Insects (%) |
| --- | --- |
| 146 | 100 |
| 147 | 100 |
| 148 | 100 |
| 149 | 100 |
| 150 | 100 |
| 151 | 100 |
| 152 | 100 |
| 153 | 100 |
| 154 | 100 |
| 155 | 100 |
| 156 | 100 |
| 157 | 100 |
| 158 | 100 |
| 159 | 100 |
| 160 | 100 |
| 161 | 100 |
| 162 | 100 |
| 163 | 100 |
| 164 | 100 |
| 165 | 100 |
| 166 | 100 |
| 167 | 100 |
| 168 | 100 |
| 169 | 100 |
| 170 | 100 |
| 171 | 100 |
| 172 | 100 |
| 173 | 100 |
| 174 | 100 |
| 175 | 100 |
| 176 | 100 |
| 177 | 100 |
| 178 | 100 |
| 179 | 100 |
| 180 | 100 |
| 181 | 100 |
| 182 | 100 |
| 183 | 100 |
| 184 | 100 |
| 185 | 100 |

What is claimed is:

1. A benzohydroximoylazole compound having the formula:

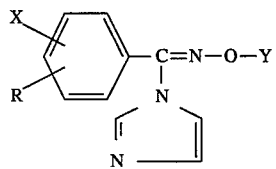

wherein

R is a branched $C_{3-8}$ alkyl group; a fluorine-substituted $C_{2-6}$ alkyl group; a branched $C_{3-7}$ alkoxy group; a halogen-substituted $C_{3-7}$ alkoxy group; a $C_{3-7}$ cycloalkyl group; a $C_{3-7}$ cycloalkylmethyl group which may be substituted with one or two methyl groups; a trimethylsilylethyl group; a silyl $C_{1-2}$ alkylyoxy group which is substituted with, independently, a $C_{1-2}$ alkyl group, a vinyl group or a chloromethyl group; a $C_{3-6}$ cycloalkyloxy group which may be substituted with one or two methyl groups; a butylthio group; a halogen-substituted $C_{4-5}$ alkoxymethyl group; a $C_{5-6}$ alkenyl group; a $C_6$ alkynyl group; or a halogen-substituted vinyloxy group;

X is hydrogen, chlorine or fluorine; and

Y is a $C_{1-4}$ alkyl group.

2. The benzohydroximoylazole compound of claim 1, wherein

R is a branched $C_{5-8}$ alkyl group; a fluorine-substituted $C_{2-6}$ alkyl group; a branched $C_{3-7}$ alkoxy group; a halogen-substituted $C_{3-5}$ alkoxy group; a $C_{3-7}$ cycloalkyl group; a $C_{4-7}$ cycloalkylmethyl group which may be substituted with one or two methyl groups; a trimethylsilylethyl group; a silyl $C_{1-2}$ alkoxy group which is trisubstituted with, independently, a $C_{1-2}$ alkyl group, a vinyl group or a chloromethyl group; a $C_{3-6}$ cycloalkyloxy group which may be substituted with one or two methyl groups; a butylthio group; a halogen-substituted butoxymethyl group; a $C_{5-6}$ alkenyl group; a $C_6$ alkynyl group; or a halogen-substituted vinyloxy group.

3. The benzohydroximoylazole compound of claim 2, wherein

R is a branched $C_{5-6}$ alkyl group; a branched $C_{4-7}$ alkoxy group; a silylmethoxy group which is trisubstituted with a $C_{1-2}$ alkyl group; or a butylthio group.

4. An insecticidal composition comprising an insecticidally effective amount of the benzohydroximoylazole compound of claim 1 and an acceptable carrier.

5. An insecticidal composition comprising an insecticidally effective amount of the benzohydroximoylazole compound of claim 2 and an acceptable carrier.

6. An insecticidal composition comprising an insecticidally effective amount of the benzohydroximoylazole compound of claim 3 and an acceptable carrier.

7. A method of killing insects comprising applying to a site infested or liable to infestation an insecticidally effective amount of the benzohydroximoylazole compound of claim 1.

8. A method of killing insects comprising applying to a site infested or liable to infestation an insecticidally effective amount of the benzohydroximoylazole compound of claim 2 and an acceptable carrier, 9. A method of killing insects comprising applying to a site infested or liable to infestation an insecticidally effective amount of the benzohydroximoylazole compound of claim 3 and an acceptable carrier.

* * * * *

UNITED STATES PATENT AND TRADEMARK OFFICE
CERTIFICATE OF CORRECTION

PATENT NO. : 5,512,551
DATED : April 30, 1996
INVENTOR(S) : Keiji TORIYABE, et al.

It is certified that error appears in the above-indentified patent and that said Letters Patent is hereby corrected as shown below:

On the title page, Item [54], the title, should read:

--BENZOHYDROXIMOYLAZOLE DERIVATIVES AND
  INSECTICIDE INCLUDING THE SAME--

Signed and Sealed this

Sixth Day of August, 1996

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   :   5,512,551
DATED:       :   April 30, 1996
INVENTOR(S)  :   Keiji TORIYABE et al It is certified that error appears in the above-identified patent and that said Letters patent is hereby corrected as shown below:

On the title page, delete Item [62] in its entirety and replace with

```
--[62] Division of Ser. No. 915,817, Pat. No. 5,366,988,
filed as PCT/JP91/01614, Nov 25, 1991.--
```

Signed and Sealed this

Twenty-fourth Day of November, 1998

*Attest:*

BRUCE LEHMAN

*Attesting Officer*   Commissioner of Patents and Trademarks